United States Patent
Zahedi (10) Patent No.: US 9,040,008 B2
(45) Date of Patent: May 26, 2015

(54) METHOD FOR REMOVAL OF PARTICLES AND VOC FROM AN AIRSTREAM

(71) Applicant: EFB, INC., Newton Center, MA (US)

(72) Inventor: Karim Zahedi, Newton, MA (US)

(73) Assignee: EFB, Inc., Newton Center, MA (US)

( * ) Notice: Subject to any disclaimer, the term of this patent is extended or adjusted under 35 U.S.C. 154(b) by 0 days.

(21) Appl. No.: 14/543,087

(22) Filed: Nov. 17, 2014

(65) Prior Publication Data

US 2015/0071842 A1    Mar. 12, 2015

Related U.S. Application Data

(62) Division of application No. 13/005,151, filed on Jan. 12, 2011, now Pat. No. 8,889,079.

(60) Provisional application No. 61/294,602, filed on Jan. 13, 2010.

(51) Int. Cl.
*B01D 53/02* (2006.01)
*A61L 9/015* (2006.01)
*B01D 53/32* (2006.01)

(52) U.S. Cl.
CPC ............... *A61L 9/015* (2013.01); *B01D 53/323* (2013.01); *Y10S 588/90* (2013.01)

(58) Field of Classification Search
USPC ........................................ 423/245.1; 588/900
See application file for complete search history.

(56) References Cited

U.S. PATENT DOCUMENTS

| | | |
|---|---|---|
| 3,269,801 A | 8/1966 | Boberg et al. |
| 3,972,979 A | 8/1976 | Kageyama |
| 4,038,036 A | 7/1977 | Beavon |
| 4,053,557 A | 10/1977 | Kageyama |
| 4,059,683 A | 11/1977 | Lindberg et al. |
| 4,206,083 A | 6/1980 | Chang |
| 4,343,776 A | 8/1982 | Carr et al. |
| 5,080,882 A | 1/1992 | Yoshimoto et al. |
| 5,187,137 A | 2/1993 | Terui et al. |
| 5,250,489 A | 10/1993 | Dalla Betta et al. |
| 5,283,041 A | 2/1994 | Nguyen et al. |
| 5,403,383 A | 4/1995 | Jaisinghani |
| 5,422,331 A | 6/1995 | Galligan et al. |
| 5,578,283 A | 11/1996 | Chen et al. |
| 5,593,476 A | 1/1997 | Coppom |
| 5,643,545 A | 7/1997 | Chen et al. |
| 5,653,949 A | 8/1997 | Chen et al. |
| 6,059,675 A | 5/2000 | Finn |
| 6,059,676 A | 5/2000 | Seymour et al. |
| 6,245,132 B1 | 6/2001 | Feldman et al. |
| 6,319,484 B1 | 11/2001 | Shore et al. |

OTHER PUBLICATIONS

Boelter et al., "Ozone Generation by Indoor, Electrostatic Air Cleaners", Aerosol Science and Technology, Jan. 1997, vol. 27, Issue 6, pp. 689-708.

*Primary Examiner* — Edward Johnson
(74) *Attorney, Agent, or Firm* — Miles & Stockbridge P.C.

(57) ABSTRACT

Apparatus and method for removal of particles and VOC from an airstream, in which particles carried by the airstream are charged by a corona ionizer and then collected by an electrically enhanced filter downstream of the ionizer. A catalytic filter downstream of the electrically enhanced filter removes VOC as well as ozone generated by the ionizer.

3 Claims, 9 Drawing Sheets

FRONT VIEW
FIG. 5B

SIDE VIEW
FIG. 5C

BACK VIEW
FIG. 5D

FIG. 6

TOP VIEW OF
V-CELL FILTER

FIG. 7A:  TOP VIEW OF ENERGIZING ELECTRODE

FIG. 7B:  SIDE VIEW OF ENERGIZING ELECTRODE

FIG. 8A: TOP VIEW    FIG. 8C: IONIZER GRID

FIG. 8B: SIDE VIEW

US 9,040,008 B2

METHOD FOR REMOVAL OF PARTICLES AND VOC FROM AN AIRSTREAM

CROSS-REFERENCE TO RELATED APPLICATION

This application takes the benefit of provisional application 61/294,602 filed Jan. 13, 2010, incorporated herein by reference.

BACKGROUND OF THE INVENTION

This invention is concerned with the purification of an airstream, more particularly for the removal of contaminants such as particles and VOC, as well as biological pollutants.

Techniques for purifying an airstream are well known, but, in general, prior techniques suffer from one or more disadvantages, including, but not limited to, inefficiency, size, cost, and longevity limitations, and undesirable by-products.

In one type of prior airstream purifier, an ionizer uses wires to charge particles in an incoming airstream, and an electric field directs the charged particles to a particle collecting filter. One problem with such purifiers is the inefficient and non-uniform generation of ions. Another problem is the premature failure of the filter. A further problem is the undesired presence of ozone in the exhaust stream of the purifier.

BRIEF DESCRIPTION OF THE INVENTION

The present invention provides improved apparatus and method for purifying an airstream that eliminates or minimizes disadvantages of prior apparatus and methods. Both contaminant particles and VOC are efficiently removed from an airstream. In a preferred embodiment, an improved corona ionizer generates a high concentration of ions to charge particles in the airstream and to generate a low concentration of ozone. An electrically enhanced media filter collects the particles, and a catalytic filter removes the VOC and the ozone. The improved ionizer produces intense ionization upstream of the ionizer while minimizing the generation of ions downstream of the ionizer.

BRIEF DESCRIPTION OF THE DRAWINGS

The invention will be further described in conjunction with the accompanying drawings, which illustrate preferred and exemplary embodiments, and wherein.

DETAILED DESCRIPTION OF THE INVENTION

Several embodiments will be described with reference to diagrammatic drawings in which spacings of parts of the invention have been shown merely for ease of illustration.

Figure 1A:
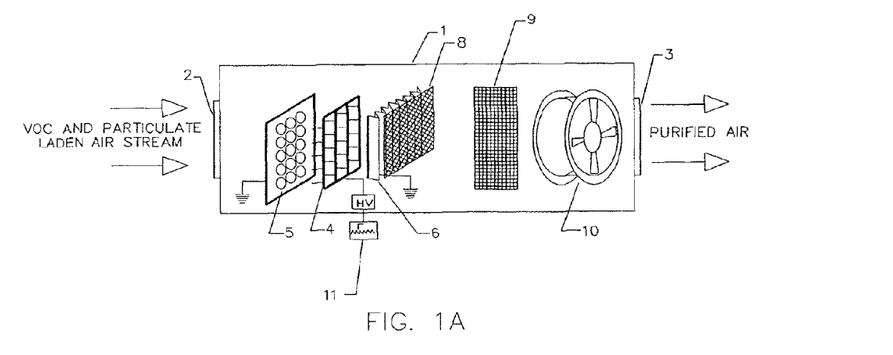
FIG. 1A is a diagrammatic view of an embodiment of the invention, in which a fan near an outlet of a housing draws air though the housing.

An embodiment of the invention shown in FIG. 1A illustrates an air purifier comprising a main housing 1 containing a passageway for air to flow through the purifier from an air inlet 2, to an air outlet 3.

Upon entering the air purifier, the airflow encounters a first electrode 5 formed by a perforated metal plate with round holes that is electrically grounded. The airflow passes through the holes and encounters a second electrode 4 comprising a plurality of sharp metal pins 4a on a metal grid 4b. Second electrode 4 constitutes an ionizer that cooperates with first electrode 5 to form a very efficient, uniform ionizing assembly.

Figure 2A:
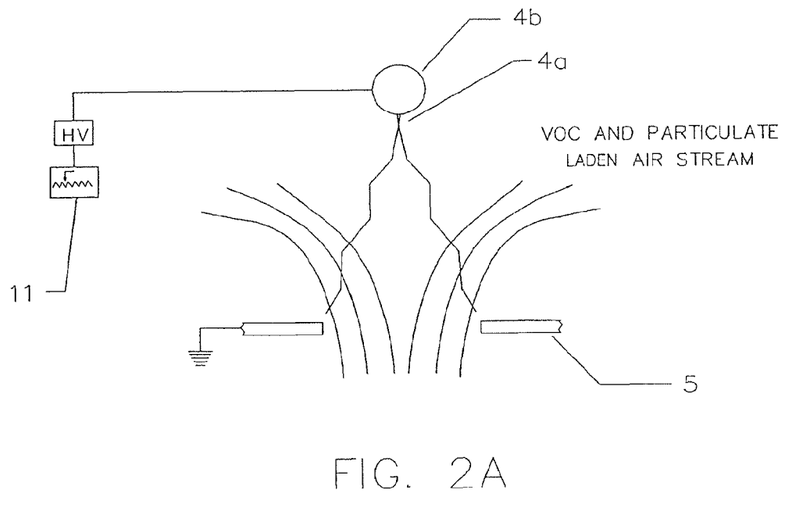
FIGS. 2A and 2B are diagrammatic views illustrating the generation of ions in an ionizer of the invention.
Figure 2B:
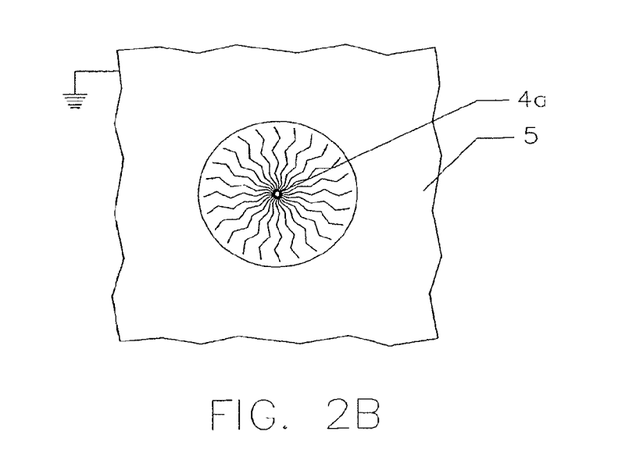
Figure 3A:
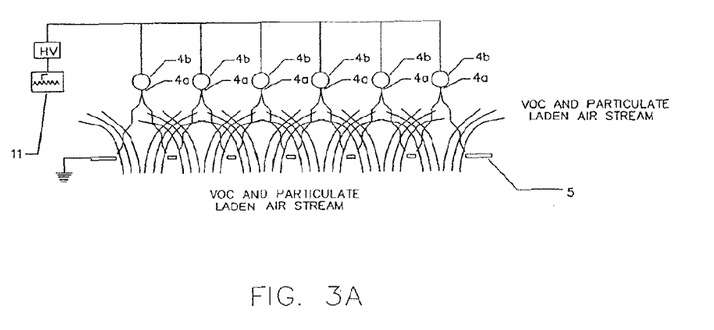
FIGS. 3A and 3B are diagrammatic views further illustrating the generation of ions.
Figure 3B:
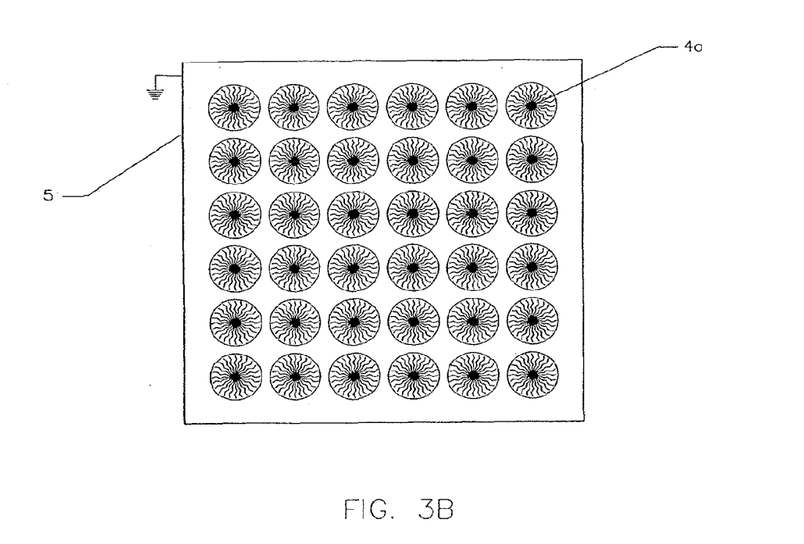

As shown in FIGS. 2 and 3, there are equal numbers of pins 4a and holes in the perforated plate 5. Each pin faces, and is centered on, a corresponding hole, and the incoming airflow is distributed uniformly though the perforated plate 5 toward the pins 4a.

The second electrode 4 is energized at a high voltage of several thousand volts (e.g., 10 to 30 KV) by means of a DC power supply 11, the voltage of which is adjustable and its polarity can be either positive or negative. As shown in FIGS. 2 and 3, a corona ionization stream is formed on the tip of each pin 4a and is directed to the circumference of the corresponding hole in plate 5, forming a cone of ionized molecules.

The particulate and VOC laden airstream passes though these conical zones and is bombarded with ions that attach themselves to particles contained in the airstream. The ionizer also generates ozone, which is capable of chemically reacting with organic molecules.

The airflow next encounters a particle collector comprising a very efficient electrically enhanced fibrous media filter 6 having a dielectric (preferably pleated) filter medium and a porous conductive material backing, such as an expanded metal sheet 8, that is grounded and that can be in direct contact with the filter media. The filter is placed downstream of the electrode 4 with an air gap (e.g., ¼ inch), so that it is not in direct contact with the electrode 4. The grid structure 4b and the grounded plate 8 impose an electric field on the filter media and polarize the fibers of the filter media. The DC high voltage power supply 11 provides a high voltage between electrode 4 and the metal plate 8. Polarized fibers of the filter media attract the charged particles in the airstream and remove them.

After leaving an electrostatic purification portion of the air purifier, just described, the airflow enters a chemical purification portion of the air purifier, comprising a catalytic filter 9, which catalytically oxidizes the VOC in the airstream by ozone, turns harmful VOC into harmless water and carbon dioxide, and decomposes the ozone. A fan 10 moves the airstream through the main housing 1 and discharges it into the environment though the air outlet 3, as purified air.

Since it is desired that the entire VOC and particulate laden airstream be treated in accordance with the invention, elements 4, 5, 6, 8, and 9 must extend transversely over the entire cross section of the flow path. The invention provides a highly uniform ionization zone across an entire cross section of gas flow to prevent areas of low ionization and lower corona activity.

Further details, principles, and advantages of the invention will now be elucidated.

The damaging effects of VOCs are numerous, ranging from minor annoyances such as eyes, nose, and throat irritation, headaches, and nausea to serious dangers such as damage to the kidneys, liver, and central nervous system. Long-term exposure to some VOCs such as benzene is known to cause cancer. Due to the possible dangers attributed to VOCs, tighter regulations have been enacted to control the emissions of these substances.

Many methods are currently used to control the release of VOCs which broadly fall under three general categories. The first category involves the recovery of VOCs, and specific examples include condensation, adsorption, and absorption. The second category is made up of methods that utilize the conversion of wastes to less harmful products, and examples include biological and UV treatment. The third category involves combustion methods, and examples are thermal incineration, flaring, and catalytic incineration or oxidation.

For an application addressed herein involving large airstreams contaminated with low concentrations of VOCs (<10 ppm) such as found in indoor environments, there are specific problems with utilizing systems based on the general categories discussed above. Methods like condensation, adsorption, and absorption work best at high concentrations of VOCs and low flow rates. Methods such as biological and UV treatment are kinetically slow. Finally, the combustion methods like thermal incineration, flaring, and catalytic incineration and catalytic oxidation are effective in removing high concentrations of VOCs from large volume airstreams but are thermodynamically inefficient. They consume fuel and require large volumes of air to be heated in excess of 300° C. to 500° C. and then cooled.

In the invention, elimination of VOC is achieved by oxidizing it into harmless gases. This is done by generating ozone to react with the VOC in the presence of a suitable catalyst, such as a MnO coated honeycomb type structure of a catalytic filter. To remove particles and protect the effective life of the catalyst, an electrically enhanced filter is utilized ahead of the catalyst. Prior ozone and VOC converters have relatively short useful lifespans due to premature poisoning of the catalyst by inorganic as well as organic species and particles that are present in an airstream and that collect on the surface of the catalyst, making the catalyst ineffective. The invention provides for the destruction of VOC in indoor environments via catalytic processes in which catalytic filters have very long effective filter lifetime while avoiding frequent filter changes. By virtue of the invention, premature failure of a catalytic filter can be prevented.

An electrostatic ionizer of the invention has the dual purpose of charging incoming particles and generating ozone. An improved electrode design provides an ionizer with an upstream ionizing side as well as a non-ionizing downstream side. This electrode provides corona ionization at its upstream side to charge the particles and produce ozone, and it provides a non-ionizing electric field toward a downstream media filter, so that its filtering capability is augmented by electrostatic forces. The ionizing electrode structure creates ionization at a lower noise level than conventional wire type ionizing electrodes.

A by-product of the ionization in ambient air is the formation of ozone, which is generated by the collision of high energy free electrons with oxygen molecules. The amount of ozone generated depends on many factors, among them the polarity of the applied voltage. It has been shown that a negative polarity ionizer will generate as much as ten times the amount of ozone as compared to a positive polarity. Therefore, depending on the amount of VOC in a specific air environment, the present invention preferably matches the generation of ozone to that required for complete catalytic oxidation of the VOC. For environments in which there is a relatively low concentration of VOC, and the approximate amounts are between 10 to 100 ppb, positive polarity high voltage is utilized to generate ozone concentration of around 50 to 200 ppb. For environments in which the VOC concentration is much higher and can reach levels of 100 ppb to 10 ppm, a negative polarity ionizer is preferred. The applied voltage and the resulting corona current can be adjusted to provide the desirable quantity of ozone. Low corona current results in lower ozone concentration, while high corona current results in higher ozone generation. In the invention, the ozone generation can be matched to a particular VOC removal application by adjusting the corona current.

Various forms of catalytic filters can be used, but the preferred form used in the invention is a catalyst carrier honeycomb type structure made from inorganic fibers. As the cell walls are composed of fibrous materials, this carrier can carry a wide variety of catalytic agents right in the structure of the walls and the spaces between the fibers. The honeycomb structure provides a filter with low pressure drop compared to other types. Commercially available honeycomb filters have cell densities from 100 cell/in$^2$ to 1,000 cell/in$^2$. Various catalytic coatings are available in the market. The preferred catalyst used in the invention is Mn oxides. The preferred cell density is in the range of 200 to 600 cell/in$^2$, which provides an adequate amount of the catalyst for applications in which the VOC concentration is less than 10 ppm. The pressure drop of such honeycomb filters depends on the thickness of the filter, which can range from 10 mm to 100 mm. In one preferred embodiment, the filter thickness is about 15 mm, where at the filter face velocity of 2 m/s, there is a pressure loss of around 40 Pa (about 4 mm $H_2O$) for cell densities of 600 cell/in$^2$.

In a preferred embodiment, the present invention utilizes a media filter downstream of a specifically designed electrode with an ionizing side and a non-ionizing side to charge the particles in the airstream and remove almost all of the particulate down to ultrafine sizes, which has the benefit of protecting the life of the catalyst filter. Without removal of charged particles by the media filter, such particles would quickly coat the catalyst surfaces and reduce the effective useful life of the catalyst filter. Therefore, it is desirable to place a very efficient media filter between the non-ionizing side of the electrode and the catalyst filter.

The filter medium is made of dielectric fibers, such as glass or synthetic fibers, preferably pleated, and is backed by a porous electrically conductive material such as an expanded metal plate, which is electrically grounded. It is preferred to utilize media filters that have relatively lower pressure drop, and with removal efficiency augmented by the application of an electrostatic field across the filter media. The electrostatically augmented filter, with the application of a DC electric field to the filter, will polarize the fibers of the filter media, thereby providing surfaces with positive and negative charges. Particles that have passed through the ionizer and have received an electrical charge of positive or negative polarity, depending on the ionizer polarity, are then attracted to the positive or negative sites on the surface of fibers and are collected at high rates.

In a preferred embodiment of the invention, the holes of the first electrode are arranged uniformly in parallel and in straight rows. Each hole has a diameter in excess of a half inch, preferably about 1 inch to 1.5 inches, with hole to hole center distance of around 1.5 inch to 2 inch. The number of holes is such as to provide an open area of around 25% to 30%.

The second electrode, downstream of the first electrode, has the very sharp pins arranged with the tip of each pin set at a distance of about 1 inch to 1.5 inches downstream of the holes of the first electrode, each pin being centered on a corresponding hole. The pins are arranged on a non-ionizing grid structure, which can be made of rods or strips of metal substantially more massive than the pins, so that they do not themselves generate ions.

The ionizing side of the grid electrode structure creates ions in a conical fashion toward the circumference of the holes. Incoming air is forced to pass through these ionized cones. Ions in the cones attach themselves to the airborne particles. The ionization of air also generates ozone which is capable of chemically reacting with the VOC. Since the air passes through the ionization section of the purifier and the particulate filter at relatively high velocity, it provides a very short time for the ozone to chemically react with the VOC in this section of the purifier, so much of the reaction occurs at the final section of the purifier, where the catalytic filter is located.

The embodiments of the invention benefit from substantially uniform ionization over substantially an entire cross section of an airstream while eliminating downstream ionization to avoid buildup of charge on filter media. Very small particles as well as microorganisms such as bacteria and viruses are eliminated by passing all these through an intense zone of ionization in order to trap the particles and microorganisms on the filter media and subject them to a high level of electric field that is effective to kill microorganisms.

Figure 8A:
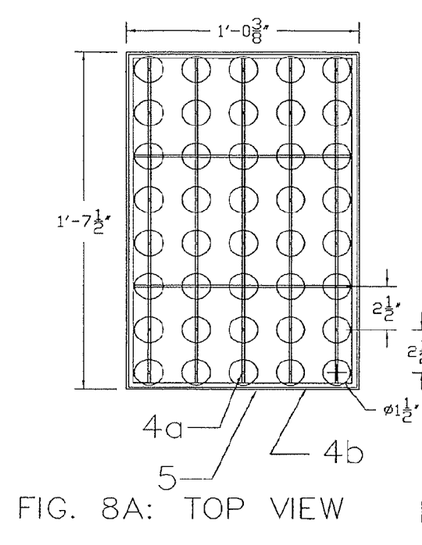
FIGS. 8A, 8B, and 8C are, respectively, a front view, a rear view, and a side view of a grid structure forming part of an ionizer of the invention.
Figure 8B:
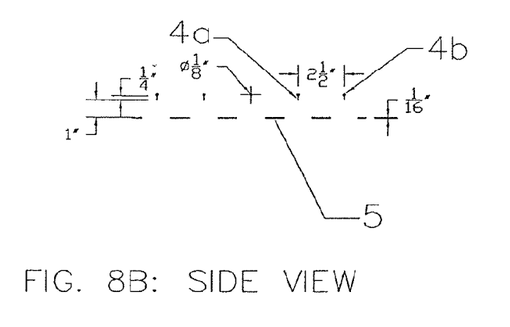
Figure 8C:
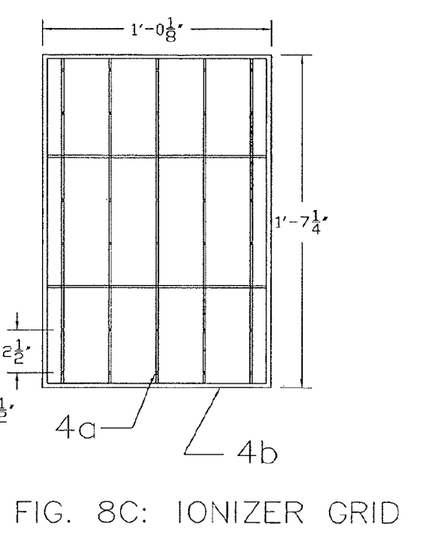

In a working embodiment of the invention, the ionizer was comprised of a grounded perforated plate 4 with approximate dimensions of 19.5 inches×12⅜ inches to allow passage of airflow with minimal restriction, with 1.5 inch diameter holes on 2.5 inch centers to form 40 holes and provide about 30% open area in the perforated plate. A grid made of ⅛ inch round rods with ¼ inch frame and mid supports was constructed as shown in FIG. 8. 40 pins were attached to the rods with a 2.5 inch spacing and at locations corresponding to the centers of corresponding holes on the perforated plate. The grid was supported on insulating walls of a main ionizer frame and was located at distance from the perforated plate 5 to set a 1 inch gap between the tip of the pins and the surface of the perforated plate 5. A DC high voltage power supply was used to provide high voltage to the ionizer grid. The polarity was set to positive polarity. The applied voltage was set to 18,000 volts, and a current of 450 microamps was established.

A pleated media filter with an expanded metal plate backing, having dimensions of 19.5 inches×12⅜ inches×2 inches thick, was placed ¼ inch downstream of the ionizer. The media was a matted glass fiber media having a Merv rating of 11, which was pleated to form 8 pleats per inch and supported in a frame with an expanded metal backing which was electrically grounded.

A catalyst filter of the honeycomb type made of non-organic fibers with cell density of 600/in$^2$ with a thickness of 15 mm and dimensions of 19.5 inches×12⅜ inches was placed immediately after the expanded metal backing. The catalyst coating on the catalytic filter was Mn oxides and was manufactured by Nichias of Japan. A fan provided approximately 200 cfm of air with pressure capability of about 15 mm H$_2$O.

The unit was placed in the middle of a room with dimensions of 12 feet by 14 feet by 9 feet, with a volume of 1,512 cubic feet. The fan was set to provide an airflow rate of 200 cfm. At this setting, about 8 air changes/hr were established. 50 ml of acetone was placed in a open dish with another 50 ml of toluene placed in another similar dish. These were placed in the middle of the room with the air purifier turned off. A mixing fan was used to mix the air in the room to provide a more uniform concentration of VOC. The VOC level was measured by a photo ionization detector. When a level of 100 ppb was established around the room, the dishes containing the VOC were removed from the room. The particle counts were also measured using a Kanomax laser particle counter. The initial particle counts were given by the counter as follows: particles smaller than 0.3 micron were counted to be 860,000/ft$^3$; particles between 0.3 micron and 5.0 micron were counted to be 136,000; and particles greater than 0.5 micron were counted to be 2,800.

Figure 9:
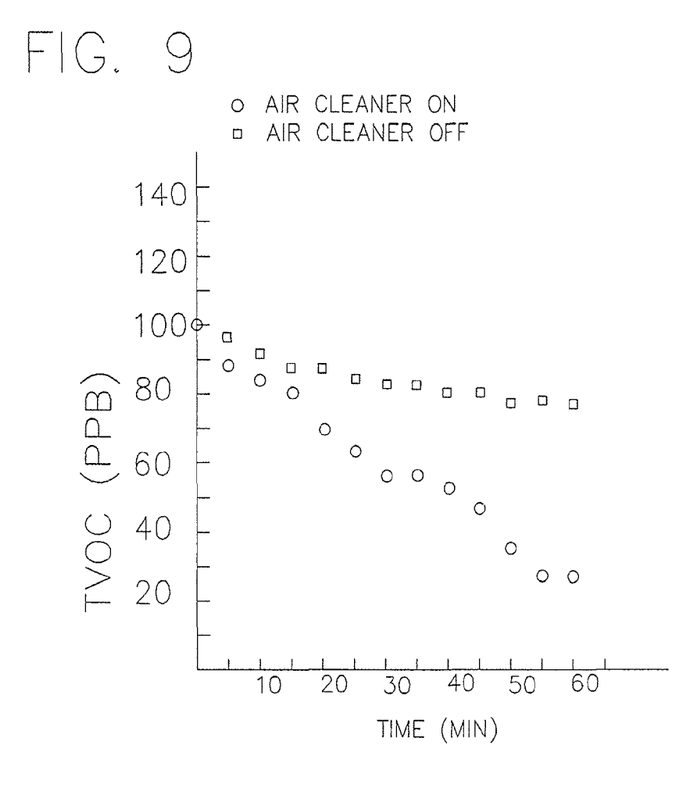
FIG. 9 is a graphical diagram illustrating the effectiveness of an air purifier in accordance with the invention.

The mixing fan was then turned off, and the air purifier was turned on for 60 minutes and the TVOC was measured every 5 minutes. The same test was conducted with the air purifier turned off for 60 minutes to obtain the natural decay of the TVOC within the room. FIG. 9 shows the results of TVOC concentration as a function of time with the air purifier on and off. Using the air purifier, the TVOC in the room came down by 40% after 30 minutes of operation and by 70% after 60 minutes of operation. The particle counts were down by 60% after 30 minutes and by 90% after 60 minutes. It was noted that the noise generated by the ionization electrode design of the invention is considerably less than the hissing noise that is produced by using a very fine wire type electrode for the ionizer.

Figure 1B:
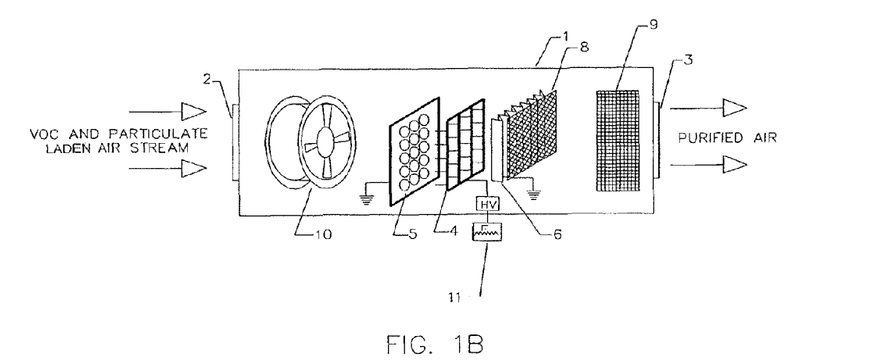
FIG. 1B is a view similar to FIG. 1A, but in which the fan is near an inlet of the housing.

In addition to the embodiment shown in FIG. 1 of the drawings, other embodiments of the invention will now be disclosed.

FIG. 1B shows a variation in which the fan 10 is placed adjacent to the inlet 2, rather than adjacent to the outlet 3. This embodiment is particularly useful with the housing and the parts contained therein oriented vertically, rather than as shown in FIGS. 1A and 1B.

Figure 4:
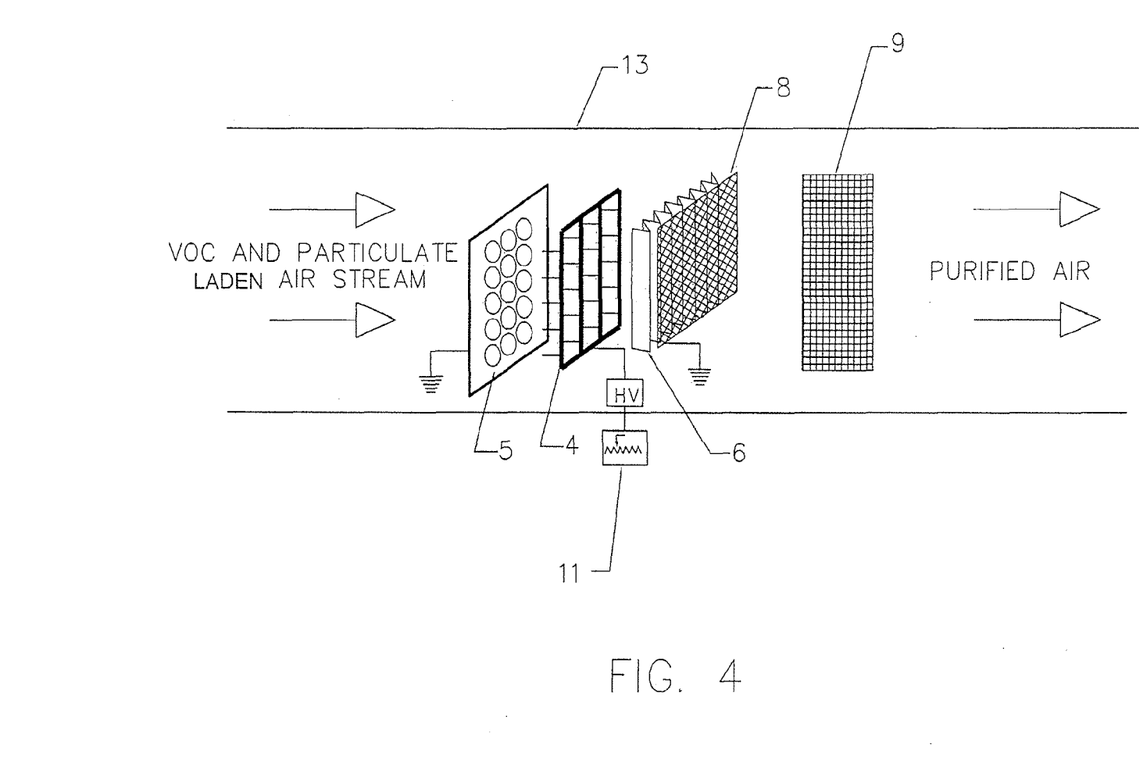
FIG. 4 is a diagrammatic view of an embodiment of the invention in which a unit of the invention is installed in ducting of an HVAC system.
Figure 5A:
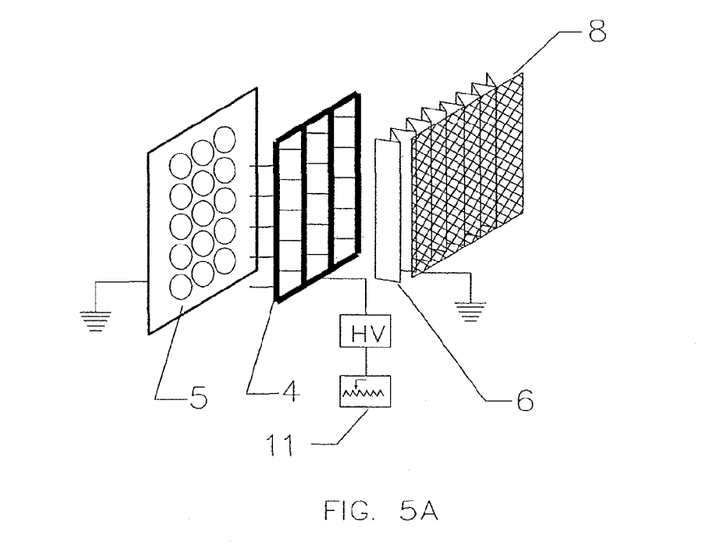
FIG. 5A is a diagrammatic view of components of a replaceable purification unit in accordance with the invention.
Figure 5B:
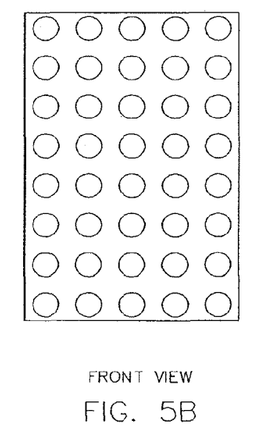
FIGS. 5B, 5C, and 5D are, respectively, a front view, a side view, and a back view of the assembled components of FIG. 5A.
Figure 5C:
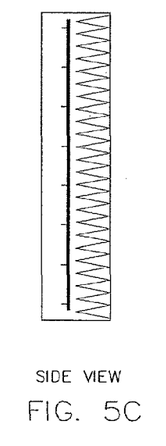
Figure 5D:
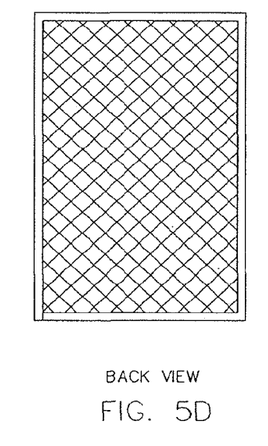

FIG. 4 shows an embodiment of the invention devoid of a housing or fan and designed for installation in the ducting 13 of HVAC systems for both residential and commercial buildings, where a central duct and fan system handle the entire air flow through the air purifier.

FIGS. 5A-5D show a replaceable ionizer and filter assembly that incorporates the ionizing electrode assembly together with the enhanced media filter assembly into one unit. Such a unit can be utilized in V-shaped filter holding racks that are generally used in large filter housings in commercial buildings. In the embodiment shown in FIGS. 5A-5D, the plate 5, the grid 4, and the plate 8 are substantially flat, with the plate 5 at one side of the unit and the plate 8 at the opposite side of the unit, and the filter medium 6 between the grid 4 and the plate 8, forming a flat box-like structure.

Figure 6:
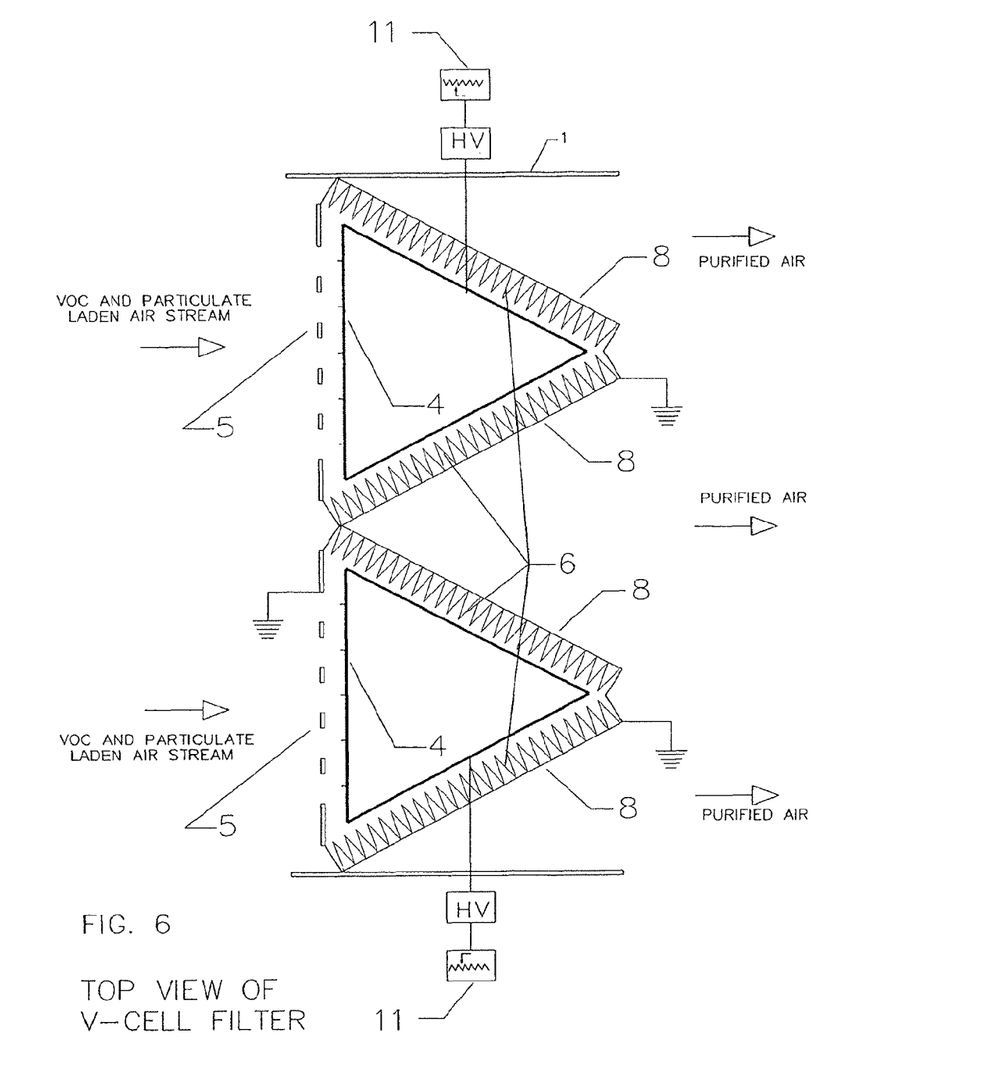
FIG. 6 is a diagrammatic view of a modification utilizing a V-pack style ionizer and filter unit of the invention.

FIG. 6 shows a filter assembly of the V-pack style, with the ionizing electrode assembly placed in the void space in front of the media filter panel sections. The media filter panel sections with the permeable metal plate 8 on the downstream side are arranged in a V-style in the filter housing. In this embodiment the grid structure 4 has a triangular configuration, with the pins projecting from one side of the triangular configuration and sections of the filter medium 6 and porous plate at remaining sides of the triangular configuration. The sections of the filter medium and the porous plate form a V-shape that opens toward the perforated plate 5. In FIG. 6 there are two V-shaped units that extend across the housing 1 transversely.

Figure 7A:
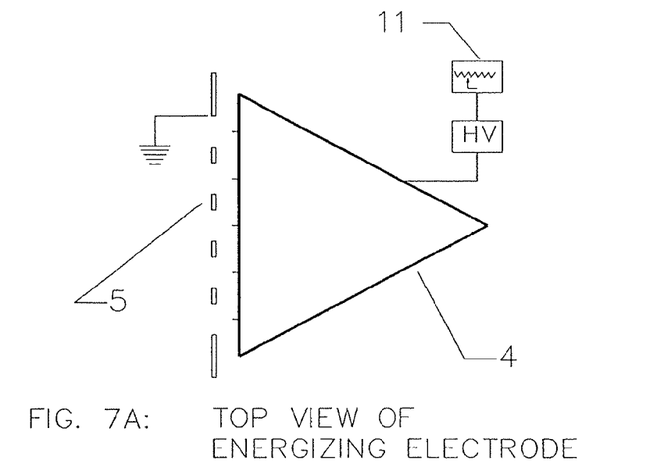
FIGS. 7A and 7B are, respectively, a diagrammatic top view and side view of an energizing electrode forming part of an ionizer of the invention.
Figure 7B:
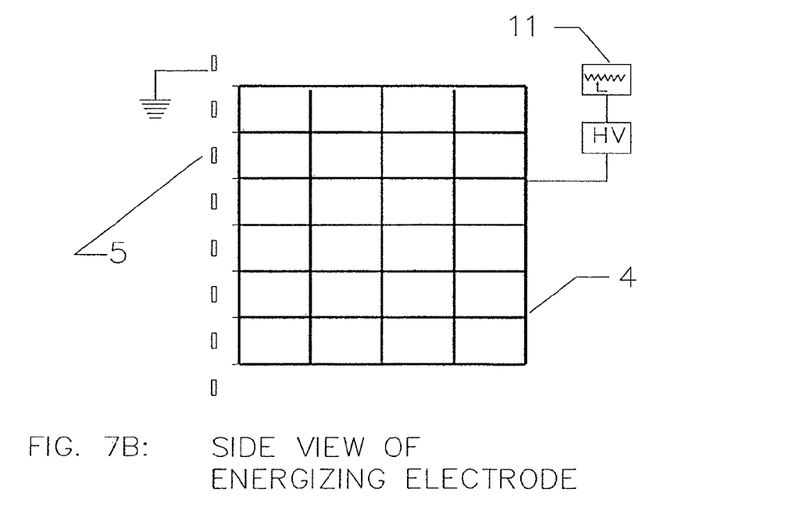

FIGS. 7A and 7B detail the triangular grid and related parts, where sharp pins are placed on the upstream section of the grid and the pins are pointed toward the perforated plate upstream. Such a V-pack style unit can be utilized individually or as multiple V-packs assembled in larger housings to handle large volumes of air in commercial buildings.

While several embodiments of the invention have been shown and described, it will be apparent that those embodiments are exemplary, rather than restrictive, and that modifications and variations can be made within the scope of the invention as defined in the appended claims. For example, the improved ionizer assembly can be used in gas streams other than air, and even in the absence of a gas stream. In some applications, other types of catalytic filters may be useful, and even other types of devices for removing VOC from an airstream.

The following references, incorporated herein by reference, provide background of the invention, prior art techniques improved by the invention, and examples of components that may be useful in the invention:

| | | | |
|---|---|---|---|
| 3,972,979 | 5,578,283 | 5,250,489 | 4,053,357 |
| 5,653,949 | 5,080,882 | 4,059,675 | 6,319,484 |
| 6,245,132 | 4,059,676 | 5,422,331 | 5,593,476 |
| 4,059,683 | 4,206,083 | 5,403,383 | 5,283,041 |
| 5,187,137 | 5,643,545 | 4,343,776 | |

Ozone Generation by Indoor, Electrostatic Air Cleaners. Kimberly J. Boeler and Jane H. Davidson. Aerosol Science and Technology, 27: 689-708 (1997)

What is claimed is:

1. A method of removing contaminant particles and VOC from an airstream, which comprises:
    generating ions to charge the particles and generate ozone,
    collecting the charged particles downstream of the generating, and
    catalytically removing VOC and ozone from the airstream downstream of the collecting of the particles.

2. A method according to claim 1, wherein the ion generating produces an intense region of ionization upstream of an ionizer while minimizing ionization downstream of the ionizer, at a region in which an electric field directs charged particles to a particle collector.

3. A method according to claim 2, wherein the particle collector uses an electrically enhanced filter.

* * * * *